United States Patent
Salla et al.

(10) Patent No.: US 8,064,983 B2
(45) Date of Patent: *Nov. 22, 2011

(54) METHOD AND SYSTEM FOR PROSPECTIVE GATING USING MULTIPLE INPUTS

(75) Inventors: Prathyusha K. Salla, Waukesha, WI (US); Gopal B. Avinash, New Berlin, WI (US); Cherik Bulkes, Sussex, WI (US)

(73) Assignee: General Electric Company, Schenectady, NY (US)

( * ) Notice: Subject to any disclaimer, the term of this patent is extended or adjusted under 35 U.S.C. 154(b) by 2011 days.

This patent is subject to a terminal disclaimer.

(21) Appl. No.: 10/723,716

(22) Filed: Nov. 26, 2003

(65) Prior Publication Data

US 2005/0113670 A1    May 26, 2005

(51) Int. Cl.
*A61B 5/05* (2006.01)

(52) U.S. Cl. ........ 600/413; 382/130; 382/131; 382/132; 600/407; 600/416

(58) Field of Classification Search .................. 600/407, 600/413, 416; 382/130, 131, 132
See application file for complete search history.

(56) References Cited

U.S. PATENT DOCUMENTS

| | | |
|---|---|---|
| 4,712,560 A | 12/1987 | Schaefer et al. |
| 4,961,426 A | 10/1990 | Spraggins et al. |
| 4,994,965 A | 2/1991 | Crawford et al. |
| 5,353,354 A | 10/1994 | Keller et al. |
| 5,363,844 A | 11/1994 | Riederer et al. |
| 5,477,144 A | 12/1995 | Rogers, Jr. |
| 5,701,897 A | 12/1997 | Sano |
| 5,810,729 A | 9/1998 | Hushek et al. |
| 5,899,861 A | 5/1999 | Friemel et al. |
| 5,997,883 A | 12/1999 | Epstein et al. |
| 6,014,473 A | 1/2000 | Hossack et al. |
| 6,144,874 A | 11/2000 | Du |
| 6,144,875 A * | 11/2000 | Schweikard et al. .......... 600/427 |
| 6,233,478 B1 * | 5/2001 | Liu ............................... 600/428 |

(Continued)

OTHER PUBLICATIONS

Yuan et al. ("Cardiac-respiratory gating method for magnetic resonance imaging of the heart", Magnetic Resonance in Medicine 43: 314-318, 2000).*

(Continued)

*Primary Examiner* — Long V. Le
*Assistant Examiner* — Ellsworth Weatherby
(74) *Attorney, Agent, or Firm* — Fletcher Yoder

(57) ABSTRACT

One or more techniques are provided for determining the overall motion of an organ of interest relative to a viewer or imager. Motion data is acquired for the organ of interest and/or for one or more proximate organs using sensor-based and/or image data-based techniques. The sensor-based techniques may include electrical and non-electrical techniques. The image data-based techniques may include both pre-acquisition and acquisition image data. The motion data for the organ of interest and proximate organs may be used to determine one or more quiescent periods corresponding to intervals of minimal motion for the organ of interest and the proximate organs. The one or more quiescent periods may be used to determine one or more gating points that may be used prospectively, i.e., during image acquisition. In addition, the one or more quiescent periods may be used to determine one or more motion compensation factors that may be used during processing and reconstruction of the acquired image data. The gating points and motion compensation factors may be used, separately or together, to reduce motion-related artifacts in the reconstructed images.

32 Claims, 5 Drawing Sheets

U.S. PATENT DOCUMENTS

| | | | |
|---|---|---|---|
| 6,278,890 | B1 | 8/2001 | Chassaing et al. |
| 6,295,464 | B1 | 9/2001 | Metaxas |
| 6,298,260 | B1 | 10/2001 | Sontag et al. |
| 6,324,254 | B1 * | 11/2001 | Pflaum ............... 378/95 |
| 6,358,208 | B1 | 3/2002 | Lang et al. |
| 6,690,963 | B2 | 2/2004 | Ben-Haim et al. |
| 6,694,166 | B2 | 2/2004 | Salome et al. |
| 6,791,323 | B2 | 9/2004 | Wang et al. |
| 6,836,529 | B2 * | 12/2004 | Li et al. ............... 378/8 |
| 2001/0031919 | A1 | 10/2001 | Strommer et al. |
| 2002/0026115 | A1 | 2/2002 | Nehrke et al. |
| 2002/0065455 | A1 | 5/2002 | Ben-Haim et al. |
| 2002/0091314 | A1 * | 7/2002 | Schlossbauer et al. ....... 600/407 |
| 2002/0156371 | A1 | 10/2002 | Hedlund et al. |
| 2002/0165446 | A1 | 11/2002 | Ryf et al. |
| 2003/0188757 | A1 | 10/2003 | Yanof et al. |
| 2004/0006266 | A1 * | 1/2004 | Ustuner et al. ............ 600/407 |
| 2004/0102695 | A1 | 5/2004 | Stergiopoulos et al. |
| 2004/0155653 | A1 | 8/2004 | Larson et al. |
| 2004/0260346 | A1 | 12/2004 | Overall et al. |

OTHER PUBLICATIONS

Yuan et al., Cardiac-respiratory gating method for magnetic resonance imaging of the heart, Magnetic Resonance in Medicine 43: 314-318, 2000.*

Huesman et al., Preliminary studies of cardiac motion in positron emission tomography, Report LBNL-41433, Lawrence Berkeley National Laboratory, Mar. 29, 2001.*

Manke et al., Novel Prospective Respiratory Motion Correction Approach for Free-Breathing COronary MR Angiography Using a Patient-Adapted Affine Motion Model, Magnetic Resonance in Medicine 50: 122-131, 2003.*

Felbinger et al., Methods and Reproducibility of Cardiac/Respiratory Double-Triggered H-MR spectroscopy of the Human Heart, Magnetic Resonance in Medicine 42: 903-910, 1999.*

Stuber et al., Submillimeter Three-dimensional Coronary MR Angiography with Real-time Navigator Correction: Comparison of Navigator Locations, Radiology, 212, 579-587, 1999.*

Huesman RH, GJ Klein, BW Reutter, and TF Budinger. Preliminary studies of cardiac motion in positron emission tomography. Report LBNL-41433, Lawrence Berkeley National Laboratory. Mar. 2001.

Leotta, Daniel F., et al., Three-Dimensional Ultrasound Imaging Using Multiple Magnetic Tracking Sensors and Miniature Magnetic Sensors, 1995, IEEE Ultrasonics Symposium.

Keegan, Jennifer, et al., Subject Specific Motion Correction Factors for Magnetic Resonance Coronary Angiography, International Workshop on Medical Imaging and Augmented Reality, pp. 67-71. 2001.

Bohning, Daryl E., et al., PC-Based System for Retrospective Cardiac and Respiratory Gating of NMR Data, Magnetic Resonance in Medicine (16), pp. 303-316. 1990.

* cited by examiner

METHOD AND SYSTEM FOR PROSPECTIVE GATING USING MULTIPLE INPUTS

BACKGROUND OF THE INVENTION

The present technique relates generally to the measurement of the overall motion undergone by an organ. More specifically, the present technique relates to measuring the motion of one or more internal organs via one or more external sensors and/or via data acquired from a medical imaging system to determine the overall motion of at least one of the internal organs.

In the medical field, it is often desirable to generate images of the internal organs or structure of a patient for diagnosis or examination. For example, magnetic resonance imaging and computed tomography are two well known examples of imaging modalities used to generate images of the internal organs or structures of a patient. The reconstructed images, however, may be flawed or contain artifacts due to the motion of internal organs, such as the heart, lungs, diaphragm, stomach, and so forth. In particular, if the imaged region has undergone motion during the imaging process, various motion related artifacts or discontinuities may be present in the reconstructed image.

To reduce or eliminate the effects of internal motion, gating techniques may be employed which utilize information about organ motion to minimize the effect of the organ motion during imaging. Gating techniques that use organ motion information to time the acquisition of imaging data are known as prospective gating techniques. Conversely, those that use organ motion information to select from image data previously acquired are known as retrospective gating techniques.

The organ motion information used for gating typically represents the contractions, convulsions, or extensions of the organ of interest. However, due to the spatial relationship of the various internal organs, many of which undergo some form of motion, gating techniques that address only a portion of the overall motion of an organ may produce images that still possess motion artifacts. For example, the rhythmic contractions of the heart, which may be determined using various techniques such as electrocardiography (ECG) or mechanical cardiography, may be used in gating the acquisition and/or reconstruction of cardiac image data. Measuring the contractions of the heart, however, only partially describes the overall motion of the heart. The motion of other organs, such as the respiratory motion of the lungs or diaphragm, may also be moving the heart relative to the viewer or imaging scanner. Consequently, knowing the cardiac motion attributable to the heart alone, such as the phase of cardiac motion, may not be sufficient to fully describe the overall motion of the heart relative to the imaging scanner, which may reduce the benefits obtainable by gating techniques. It may, therefore, be desirable to more fully characterize the motion undergone by an internal organ during imaging for purposes of gating or motion correction.

BRIEF DESCRIPTION OF THE INVENTION

The present invention is directed to a technique for detecting and/or measuring the overall motion of one or more organs of interest. The overall motion of the organ or organs of interest may be determined from a set of multi-input motion data. The multi-input motion data may comprise motion data for the organ of interest derived from multiple sources, such as sensor-based or image-data based sources. The multi-input motion data may also comprise motion data for proximate organs, which contribute to the overall motion of the organ of interest, derived from one or more sources, including possibly a source used to measure the motion of the organ of interest. The multi-input nature of the multi-input motion data, therefore, may describe either the presence of motion data for more than one organ, the presence of multiple sources of motion data for an organ, or the presence of both multi-input and multi-source motion data.

The multi-input motion data may be used to determine one or more quiescent periods for the organ of interest corresponding to an interval of minimal absolute motion for the organ. A quiescent period may be used to determine gating points that may be used to gate the image data, prospectively and/or retrospectively, to reduce motion artifacts in the resulting image. In addition, a quiescent period may be used to derive one or more motion compensation factors which may be applied during image processing to reduce motion artifacts. Alternatively, another period of motion for the organ may be derived from the multi-input motion data, such as a particular phase of motion associated with a motion cycle or period, such as the initiation of cardiac contraction.

In accordance with one aspect of the present invention, a technique is provided for imaging an organ. In view of this aspect, a set of motion data may be acquired for two or more organs from at least one of one or more types of electrical sensors and one or more types of non-electrical sensors. The set of motion data may be processed to extract two or more prospective gating points for an organ of interest. A set of image data representative of the organ of interest may be acquired using the two or more prospective gating points. Systems and computer programs that afford functionality of the type defined by this method are also provided by the present technique.

In accordance with another aspect of the present invention, a technique is provided for imaging an organ. In view of this aspect, a set of motion data may be acquired for one or more organs from at least two of one or more types of electrical sensors and one or more types of non-electrical sensors. The set of motion data may be processed to extract two or more prospective gating points for an organ of interest. A set of image data representative of the organ of interest may be acquired using the two or more prospective gating points. Systems and computer programs that afford functionality of the type defined by this method are also provided by the present technique.

BRIEF DESCRIPTION OF THE DRAWINGS

The foregoing and other advantages and features of the invention will become apparent upon reading the following detailed description and upon reference to the drawings in which.

DETAILED DESCRIPTION OF SPECIFIC EMBODIMENTS

In the field of medical imaging, it is often desirable to characterize the motion of an imaged organ so that the motion may be accounted for to improve image quality. Measures of the muscular activity of the organ of interest, however, may characterize only a portion of the overall motion of the organ relative to the viewer or imaging scanner. In particular, the overall motion may consist of not only the muscular contractions of the organ of interest itself, i.e., the inherent motion, but also motion attributable to the movement of proximate organs. For example, the overall motion of the heart may consist of not only the muscular contractions of the heart but also the movement of the lungs, the movement of the diaphragm, or other proximate muscular contractions, voluntary and/or involuntary, of the patient's body. Therefore, in the example of cardiac imaging, it may be desirable to characterize the overall motion of the heart relative to the imager, not simply the motion attributable to the contraction of the heart itself.

For example, the motion of the organ to be imaged may be used in image acquisition or reconstruction techniques that rely on data gating. In general, data gating techniques acquire image data (prospective gating) or select acquired image data (retrospective gating) based upon the motion of the organ being imaged, allowing image data to be acquired or selected at or near the desired phase of motion. The acquired or selected image data may then be reconstructed to form images that have fewer artifacts attributable to organ motion.

However, to the extent that the gating process relies only upon information related to the muscular contraction or movement of the organ of interest, the process may not account for the motion component attributable to other proximate organs. In other words, the overall motion of the organ of interest may not be accounted for by looking at the muscular activity of the organ of interest alone. Failure to account for the overall motion of the organ of interest during gating may result in reconstructed images containing motion related artifacts.

One way in which the overall motion of the organ of interest may be determined is to employ one or more motion determination techniques capable of determining the motion of the organ of interest more precisely and/or to determine the motion of one or more proximate organs that contribute to the overall motion of the organ of interest. These multiple inputs of motion data may be analyzed, such as by various combination and/or separation techniques, to determine one or more quiescent periods for the organ of interest in which the overall motion of the organ is minimized relative to the imager. The quiescent periods may then be used to gate the imaging process, either prospectively or retrospectively, to generate images of the organ of interest with reduced or minimal motion artifacts.

Figure 1:
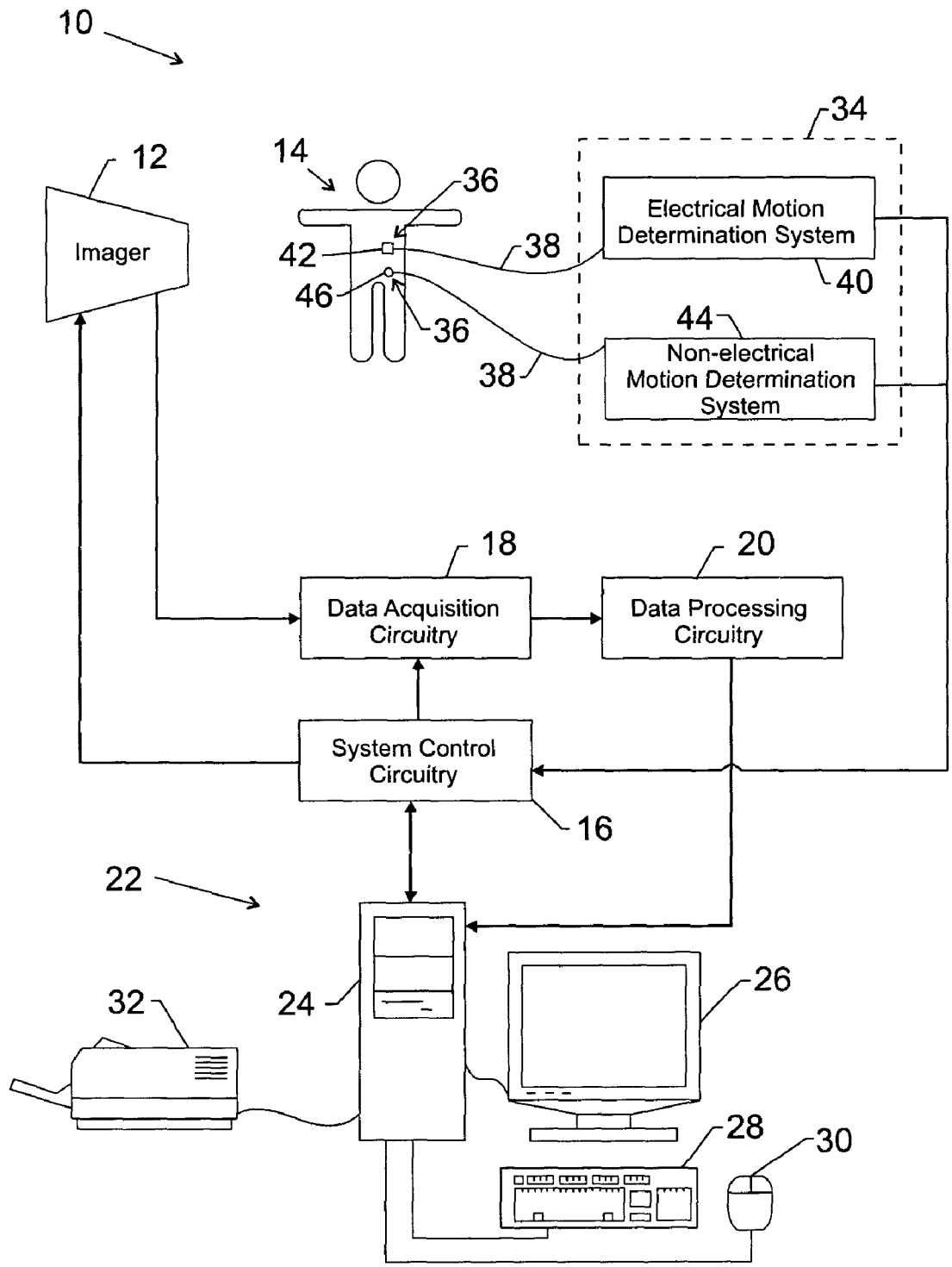
FIG. 1 is a general diagrammatical representation of certain functional components of an exemplary generic imaging system capable of gating and/or motion correction via the present technique.

An exemplary imaging system 10 capable of operating in accordance with the present technique is depicted in FIG. 1. Generally, the imaging system 10 includes some type of imager 12 that detects signals and converts the signals to useful data. As described more fully below, the imager 12 may operate in accordance with various physical principals for creating the image data. In general, however, the imager 12 creates image data indicative of the region of interest in a patient 14, either in a conventional support, such as photographic film, or in a digital medium.

The imager 12 operates under the control of system control circuitry 16. The system control circuitry 16 may include a wide range of circuits, such as radiation source control circuits, timing circuits, circuits for coordinating data acquisition in conjunction with patient or table movements, circuits for controlling the position of radiation sources and detectors, and so forth. In the present context, the system control circuitry 16 may also include memory elements, such as magnetic or optical storage media, for storing programs and routines executed by the system control circuitry 16 or by associated components of the system 10. The stored programs or routines may include programs or routines for performing all or part of the present technique.

Image data or signals acquired by the imager 12 may be processed by the imager 12, such as for conversion to digital values, and provided to data acquisition circuitry 18. The data acquisition circuitry 18 may perform a wide range of processing functions, such as adjustment of digital dynamic ranges, smoothing or sharpening of data, as well as compiling of data streams and files, where desired. In situations where pre-acquisition image data, such as Navigator pulses in magnetic resonance imaging (MRI), are acquired, the data acquisition circuitry 18 may provide image data to the system control circuitry 16 for prospective gating.

The data acquisition circuitry 18 may also transfer acquisition image data to data processing circuitry 20, where additional processing and analysis are performed. The data processing circuitry 20 may perform substantial analyses of image data, including ordering, sharpening, smoothing, feature recognition, and so forth. In addition, the data processing circuitry 20 may receive motion data for one or more organs from one or more sensor-based motion detection systems 34, as discussed in detail below. Based on image-based and/or sensor-based motion data, gating and/or motion compensation may be facilitated by the data processing circuitry 20, such as by determining gating intervals and/or motion corrections factors that may be provided to the system control circuitry 16 and/or operator workstation 22. The processed image data may be stored in short or long term storage devices, such as picture archiving communication systems, which may be located within or remote from the imaging system 10 and/or reconstructed and displayed for an operator, such as at the operator workstation 22.

In addition to displaying the reconstructed image, the operator workstation 22 may control the above-described operations and functions of the imaging system 10, typically via an interface with the system control circuitry 16. The operator workstation 22 may include one or more processor-based components, such as general purpose or application specific computers 24. In addition to the processor-based components, the operator workstation 22 may include various memory and/or storage components including magnetic and optical mass storage devices, internal memory, such as RAM chips. The memory and/or storage components may be used for storing programs and routines for performing the techniques described herein that are executed by the operator workstation 22 or by associated components of the system 10. Alternatively, the programs and routines may be stored on a computer accessible storage and/or memory remote from the operator workstation 22 but accessible by network and/or communication interfaces present on the operator workstation 22.

The operator workstation 22 may also comprise various input/output (I/O) interfaces, as well as various network or communication interfaces. The various I/O interfaces may allow communication with user interface devices, such as a display 26, keyboard 28, mouse 30, and printer 32, that may be used for viewing and inputting configuration information and/or for operating the imaging system 10. The various network and communication interfaces may allow connection to both local and wide area intranets and storage networks as well as the Internet. The various I/O and communication interfaces may utilize wires, lines, or suitable wireless interfaces, as appropriate or desired.

As one of ordinary skill in the art will appreciate, more than a single operator workstation 22 may be provided for an imaging system 10. For example, an imaging scanner or station may include an operator workstation 22 which permits regulation of the parameters involved in the image data acquisition procedure, whereas a different operator workstation 22 may be provided for manipulating, enhancing, and viewing results and reconstructed images.

The motion of one or more organs of interest may be detected and/or measured in a variety of ways and provided to the imaging system 10. As one of ordinary skill in the art will readily apprehend, the type of data gating desired may determine the type of motion data acquired. In some cases, the motion data of interest may be derived using the image scanner 12 itself. For example, pre-acquisition imaging techniques, such as navigator pulses in MR systems, scout images in CT systems or fluoroscopic images in other generalized X-ray applications, may be employed to determine the motion of the organ of interest or other organs proximate to the organ of interest. In other cases, motion data for the organ or organs of interest may be determined from the acquisition image data in the acquired, i.e., unreconstructed, domain and/or in the reconstructed domain. Use of the imaging system 10 to acquire motion data, both in the pre-acquisition and the acquisition context, are examples of image-based motion detection and measurement, as discussed in detail herein.

In some instances, however, sensor-based motion determination techniques may be employed. In these instances, the exemplary imaging system 10 may include or may be in communication with one or more sensor-based motion determination systems 34. The sensor-based motion determination systems 34 typically comprise one or more sensors 36 in the form of a pad or contact that may be disposed on skin surface of the patient 14. The contact area of a sensor 36 may vary in size from micrometers to centimeters in diameter and height. The size selected is usually based on an application. Similarly, the number of sensors 36 used may depend on the application.

When disposed on the patient 14, the sensor 36 may detect and/or measure some metric or parameter of interest, such as an electrical or mechanical event, that may be used as an indicator of organ motion. The sensor 36 may be connected to the respective sensor-based determination system 34 via one or more leads 38 which may transmit a signal representative of the sensed metric or parameter to the respective system 34 for processing. In some contexts, the sensor 36 may communicate with the respective sensor-based motion determination system 34 via wireless means, such as a wireless network protocol, as opposed to a physical lead 38.

Sensor-based determination systems 34 may include electrical motion determination systems 40, such as systems that detect or measure electrical activity or characteristics of an organ to indicate motion. Electrical motion determination systems 40 may measure electrical activity indicative of the muscular contractions of an organ, such as an electrocardiogram (ECG). Electrical motion detection systems 40 may also measure changes in electrical properties, such as impedance, which are indicative of organ motion, such as impedance plethysmography. The electrical sensors 42 used to detect electrical events, such as electrical contact pads, are typically strategically placed to detect the electrical attributes of the organ. For example, in the context of detecting and monitoring the motion of the heart, electrical events can be detected by a four-sensor ECG system, a twelve-sensor ECG system, a vector cardiography (VCG) type of arrangement, or by multiple ECG sensors arranged in array or matrix format to cover the region of interest.

Sensor-based motion determination systems 34 may also include non-electrical motion determination systems 44, such as systems that detect and/or measure displacement, acceleration, velocity, pressure, and/or other mechanical indicators of motion. Various types of mechanical sensors 46 may be employed to detect and/or measure the mechanical indicators of motion, including accelerometers, optical markers, displacement sensors, force sensors, ultrasonic sensors, strain gauges, photodiodes, and pressure sensors.

The non-electrical events may be detected by one or more mechanical sensors 46. In the case of multiple mechanical sensors 46, the mechanical sensors 46 may be arranged in an array or matrix format placed in or near the region of interest. Sensor arrays or configurations are possible in which the mechanical sensors 46 are arranged in a three-dimensional matrix such that the entire body surface in the region of interest is covered, such as by using a suit or wrap. Typically, in an array of mechanical sensors 46 used to measure non-electrical events, the mechanical sensors 46 are placed equidistant from each other. For instance, a $\delta$ unit of separation may be maintained between the mechanical sensors 46 in the X, Y, and/or Z directions.

In general, the mechanical sensors 46 of a non-electrical motion determination system 44 detect the mechanical, i.e., physical, motion of the organ or organs of interest via one or more of the means listed above. For example, internal movement, such as a heart beat or respiration, may create mechanical motion detectable by one or more mechanical sensors 46 disposed on the skin of the patient 14 as pressure, displacement, acceleration, and so forth. In this manner, internal motion of one or more internal organs may be detected, measured, and represented, either as a map of surface motion or as a map of internal motion. Such a map of surface or internal motion may be combined with other sensor or image data to generate a fusion image representing the various measured characteristics, such as structure, acceleration displacement, and/or electrical activity.

Figure 2:
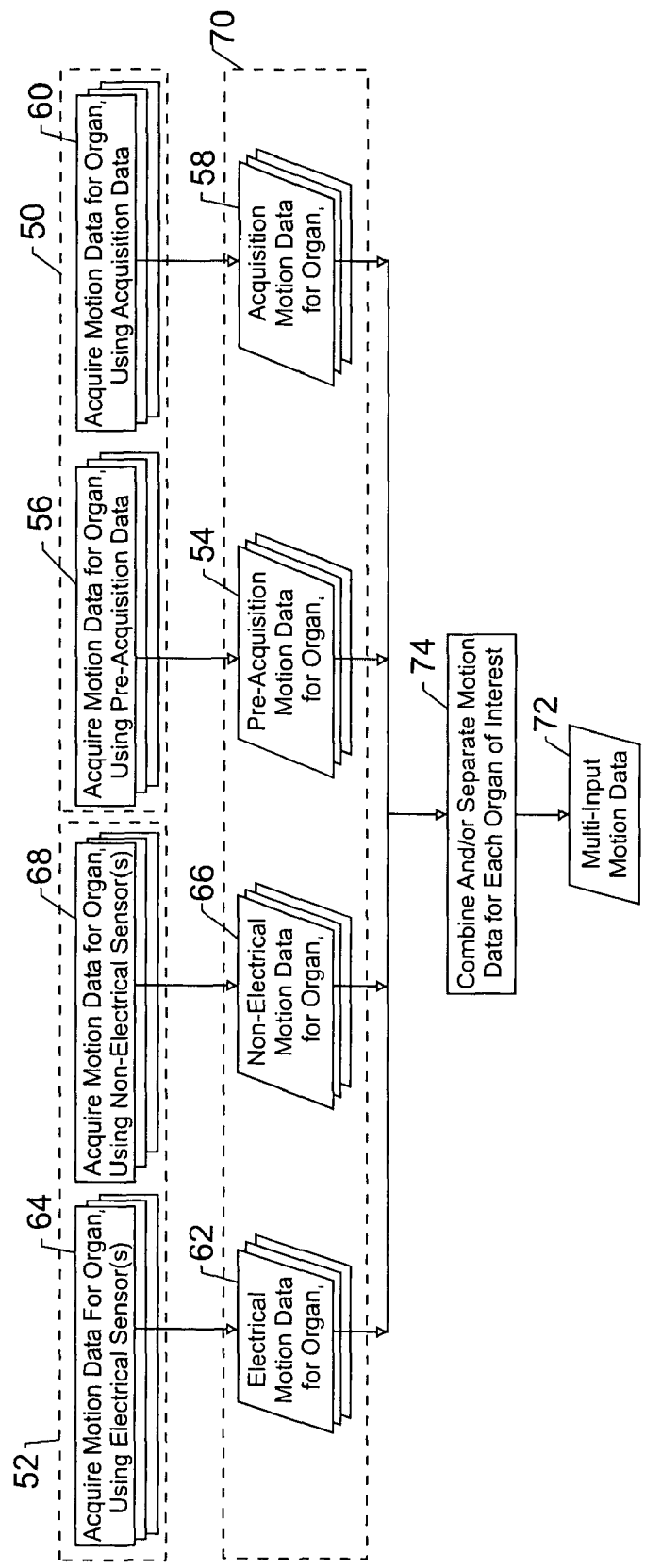
FIG. 2 is a flowchart depicting the acquisition of data representing the motion more than one organ, in accordance with the present technique.

Image-based and sensor-based motion detection and measurement using the various systems and components of FIG. 1, is described in detail with reference to FIG. 2. Detection and/or measurement of the motion of one or more organs may occur via a variety of processes and at different times prior to, during or after the imaging process. In particular, image-based detection and/or measurement of organ motion, as depicted by block 50, and/or sensor-based detection and/or measurement of organ motion, as depicted at block 52, may occur at suitable times within the process. Due to this time independence, the various motion measurement and/or detection techniques may be performed in a variety of orders or concurrently, depending on the constraints of the technique, with the resulting motion data representing the data available at any given time. For example, within the category of image-based techniques 50, motion may be detected and/or measured by using pre-acquisition motion data 54, as determined at block 56, and/or by using acquisition motion data 58, as determined at block 60.

Examples of pre-acquisition techniques for detecting or measuring motion of one or more organs, as depicted at step 56, include the use of navigator echoes in MRI, the use of scout images in CT, and the use of fluoroscopic images in other X-ray contexts. Pre-acquisition motion detection and measurement typically involves determining the position of the organ or organs of interest by a pre-acquisition measurement using the imaging system 10. Subsequent image acquisition can then occur during similar states of organ motion or subsequently acquired image data may be selected for processing and reconstruction based upon a similar state of organ motion.

For example, in MRI, a navigator echo pulse is a quick MR pre-pulse sequence that measures the position of an organ, such as the diaphragm, before primary image data acquisition. The pre-pulse sequence images a narrow area perpendicular to the movement of the organ of interest, i.e., a vertical area for a diaphragm. The contrast of the moving interface is typically high to permit easy automatic detection. Once the pre-acquisition motion data 54 has been acquired, the position of the interface may be recorded and imaging data may be acquired or selected based on whether the position of the interface falls within a range of pre-specified values determined from the pre-acquisition data 54. Using the navigator echo data, similar respiratory rates or other motion states of the patient can be identified and used for motion estimation. Hence, the navigator echo technique may be used as a respiratory gating technique that does not utilize additional sensing equipment, as the MR system itself provides the sensing.

Similarly, acquisition motion data 58, such as organ motion information derived from the acquired and/or reconstructed image domains, may be used to determine the motion of one or more organs. The acquisition motion data 58 may be determined from one-dimensional, two-dimensional, or three-dimensional representations of the imaged region derived from the image data. For example, organ motion may be determined in the acquired image domain after a segmentation or structure identification step. Changes in the location of the segmented structure or region may be determined in sequential image data and equate to the motion of the organ or organs. In this manner, acquisition motion data 58 may be used to determine motion for one or more organs in the field of view of the imager 12.

Likewise, within the category of sensor-based techniques 52, motion of one or more organs may be determined using electrical motion data 62, as determined at block 64, and/or by using non-electrical motion data 66, as determined at block 68. The electrical motion data 62 may include ECG data if the heart is an organ of interest, or impedance plethysmography data if the lungs are an organ of interest. Electrical signals or properties of other organs of interest may also comprise the electrical motion data provided suitable electrical sensors 42 are disposed on the patient 14.

In regard to non-electrical motion data 66, the motion of virtually any organ may generate mechanical or physical indicia that may be detected or measured by suitable mechanical sensors 46 disposed on the skin of the patient 14. For example, accelerometers may comprise the mechanical sensors 46 for measuring acceleration, and the respective displacement, resulting from the motion of an internal organ, such as the heart, lungs, stomach, liver, pancreas, and so on. Similarly, ultrasonic sensors, optical markers, strain gauges, and so forth may be deployed as mechanical sensors 46 suitable for measuring acceleration, displacement, velocity, pressure, and other non-electrical motion data 62 associated with one or more organs.

The aggregate motion data 70, i.e., the motion data for each organ for which motion was detected or measured and/or for each motion sensing methodology employed, contains the multi-input motion data 72 of interest for the imaging process. Aspects of the aggregate motion data 70 may be combined and/or separated for each organ of interest or for the different motion sensing methodologies, as depicted at block 74, to derive the multi-input motion data 72 relevant for the organ or organs of interest at a given time or point in the process. The combination and/or separation procedure depicted may depend on the number of organs of interest, the techniques employed to measure motion, the coverage area of the imaging modality, the processing techniques to be employed, i.e., prospective and/or retrospective, and so forth. For example, where the motion of an organ is measured or detected by multiple motion sensing methodologies, the motion information may be combined to derive a more accurate motion characterization of the organ at a given time. Similarly, where a motion sensing methodology detects the motion of more than one organ, the information associated with each organ may be separated to better characterize the motion of the individual organs at a given time. The result of the combination and/or separation procedure 74 is one or more sets of multi-input motion data 72 which may be used for motion compensation in respective images and/or may be subsequently analyzed to obtain prospective or retrospective gating intervals for image acquisition and processing.

In this manner, the multi-input motion data 72 may comprise motion data for the organ of interest derived from multiple sources, such as sensor-based or image-data based sources. The multi-input motion data may also comprise motion data for proximate organs, which contribute to the overall motion of the organ of interest, derived from one or more sources, including possibly a source used to measure the motion of the organ of interest. The multi-input nature of the multi-input motion data, therefore, may encompass either the presence of motion data for more than one organ, the presence of multiple sources of motion data for an organ, or the presence of both multi-organ and multi-source motion data.

Furthermore, positional information may be taken into account, such as during data acquisition, combination and/or separation, or during subsequent processing, to generate the multi-input motion data 72. For example, an initial determination may be made whether the coverage area of the sensors 36 or of the imager 12 is sufficient to cover the desired region of interest. If the coverage area is sufficient, motion detection and/or measurement and image processing may proceed as discussed above.

However, if the coverage area is insufficient, such as when scans or images are being taken of the torso from the neck to the abdomen or of the whole body, positional sensors may be employed. The positional sensors may provide information concerning the region being currently scanned so that other data acquisition activities may be activated or deactivated accordingly. For example, when positional sensors are employed, the sensors 36 in the area being scanned by the imager 12 may be activated while sensors 36 outside of the scanned area may remain inactive. In this manner, unnecessary or redundant data is not acquired. As one of ordinary skill in the art will appreciate, the number of positional sensors may vary depending on the application. Alternatively, the sensors 36 may all be active during the image data acquisition. The positional information obtained by the positional sensors, however, may be employed during the combination and/or separation step 74, or during subsequent processes, to discard unnecessary image or motion data or to otherwise account for the positional information during imaging.

Figure 3:
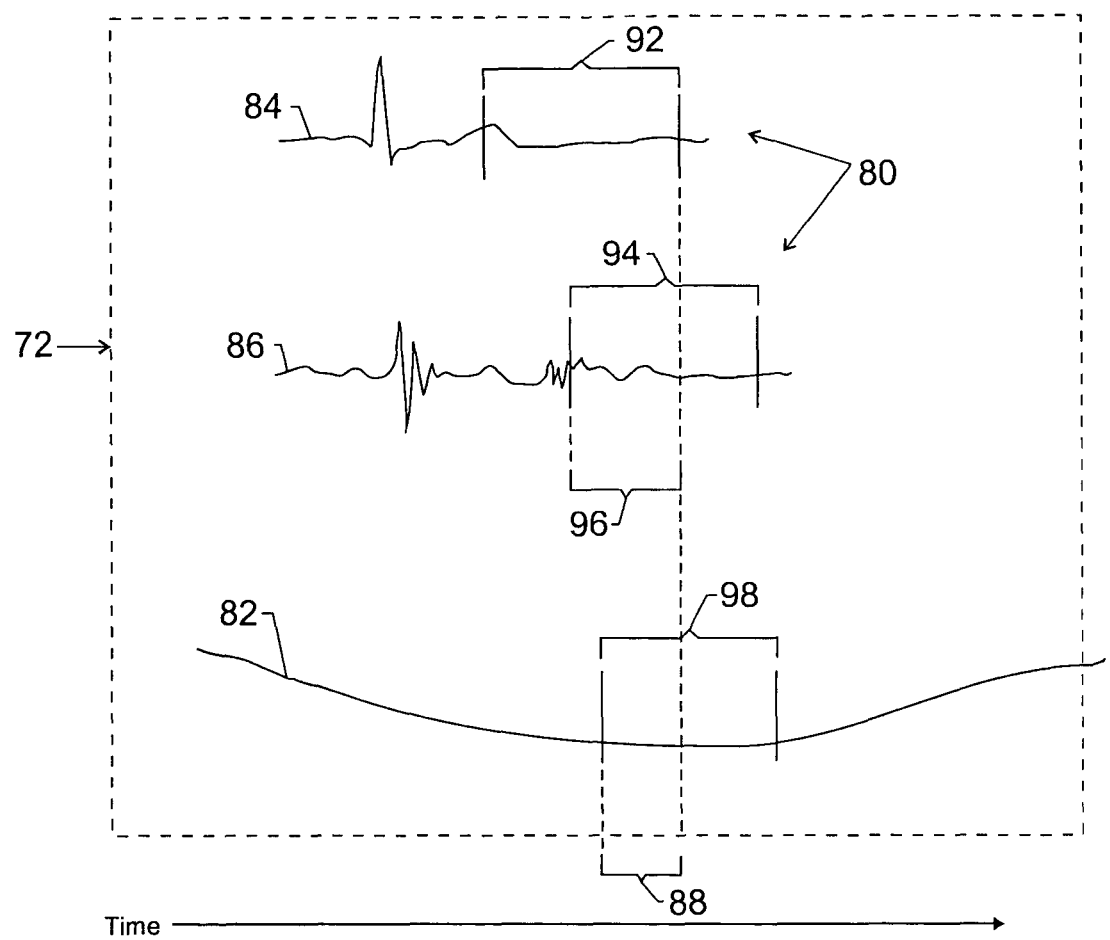
FIG. 3 is an exemplary representation of a multi-input motion data set and of a common gating period derived from the multi-input motion data.

An example of a set of multi-input motion data 72 is depicted in FIG. 3. As depicted in FIG. 3, the multi-input motion data 72 includes three waveforms, two cardiac motion waveforms 80 and a pulmonary motion waveform 82. The cardiac waveforms include an ECG 84 and a mechanical cardiogram (MCG) 86, such as may be derived using one or more mechanical sensors 46 disposed on the skin that measure cardiac acceleration and/or displacement. The pulmonary motion waveform 82 may be derived by electrical means, such as impedance plethysmography, or by non-electrical means, such as by the acceleration or displacement measured by one or more mechanical sensors 46. Indeed, the same mechanical sensors 46 may be used to measure both heart and lung motion with the motion data associated with each organ being separated to form the multi-input motion data 72.

Figure 4:
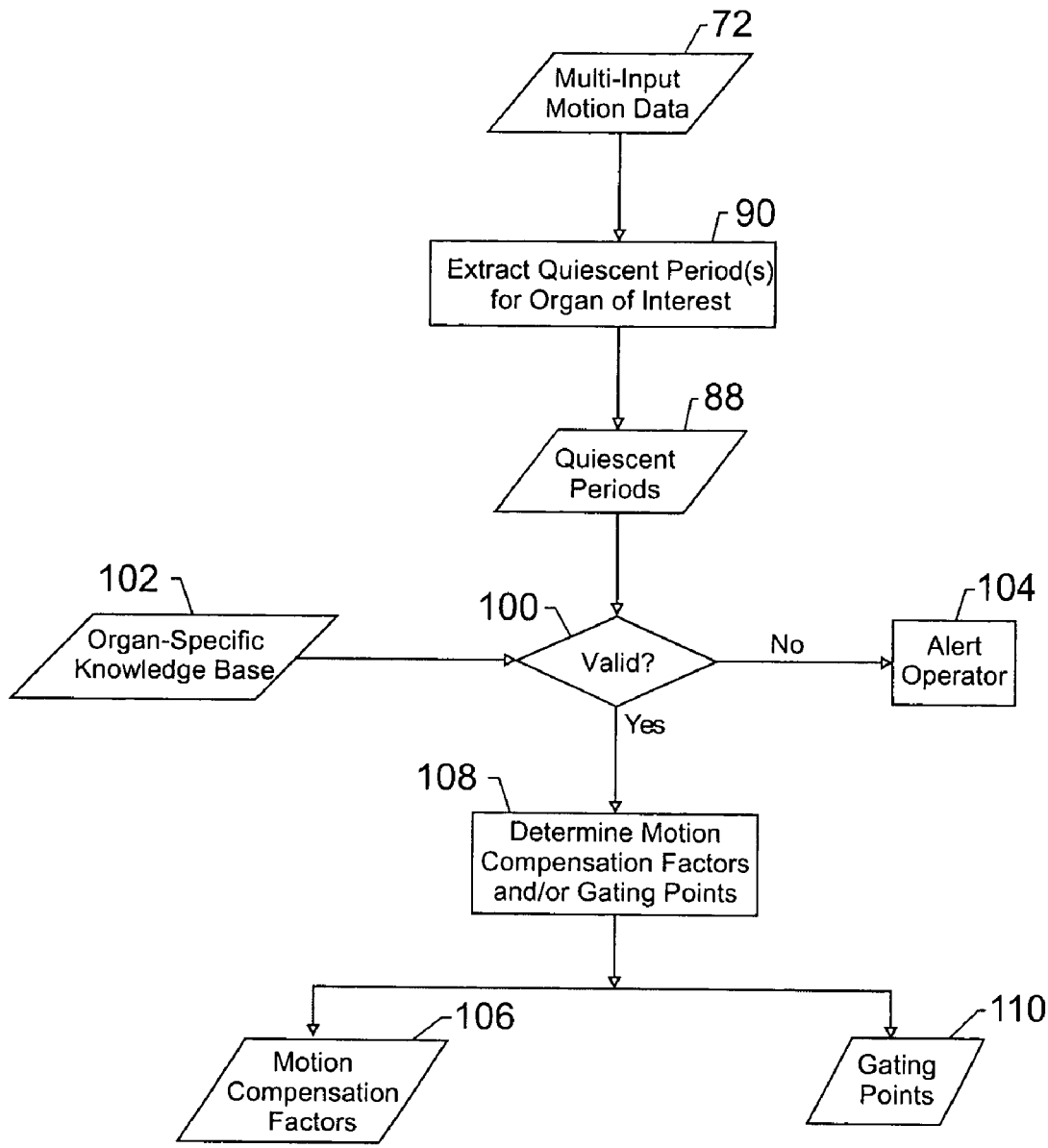
FIG. 4 is a flowchart depicting the determination of gating points and/or motion compensation factors from a set of multi-input motion data.

In the context of gating techniques, the multi-input motion data 72 may be processed to extract one or more quiescent periods 88 for the one or more organs of interest, as depicted at step 90 of FIG. 4. Referring once again to FIG. 3, this extraction process can be visualized with reference to the cardiac waveforms 80 and the pulmonary waveform 82. For example, referring to the ECG waveform 84, an interval of minimal motion 92 can be distinguished from the ECG 84 between the T wave and the subsequent P wave. Similarly, an interval of minimal motion 94 can be distinguished from the MCG 86 roughly coincident with the interval 92 determined from the ECG 84. A cardiac interval of minimal motion 96 which reflects the interval common to the ECG interval 92 and the MCG interval 94 can thereby be derived from the cardiac waveforms 80. Similarly, a pulmonary interval of minimal motion 98 can be derived from the pulmonary waveform 82.

A quiescent period 88 that reflects the interval common to the cardiac interval of minimal motion 96 and the pulmonary interval of minimal motion 98 may thereby be derived. In the context of the present example, the quiescent period 88 represents an interval of minimal motion for all of the organs represented by the multi-input motion data 72. As one of ordinary skill will appreciate, additional quiescent periods 88 may be similarly derived. Furthermore, additional motion data for these organs and/or for other or additional organs may be included within the multi-input motion data 72. In particular, the generation and/or processing of the multi-input motion data set 72, such as in the separation/combination step 74 and/or in the extraction step 90, can be performed for each individual organ separately, in series, in parallel, or in any order for use in subsequent processes and analyses.

As a validation step or as an additional step in the process, the organ motion from a second source, such as from motion computed in either one-dimension or two-dimensions from the unreconstructed or reconstructed acquisition image data may be used for validation. In this manner, organ motion derived from the acquisition image data can be synergistically used to determine one or more quiescent periods 88 or to validate the quiescent periods 88 determined by sensor-based and/or pre-acquisition image data-based techniques, as depicted at decision block 100. In addition, the one or more quiescent periods 88 may be tested for validity based on organ specific knowledge 102 pertaining to the one or more organs of interest, such as may be obtained from a general physiological reference work or database, or based on patient specific factors, such as patient history. If the quiescent period 88 is determined not to be valid based on the image-based motion information and/or the organ or patient specific knowledge, an operator may be alerted that no quiescent period 88 can be extracted, as depicted at block 104, and acquisition or processing may be terminated or modified.

If the one or more quiescent periods 88 are determined to be valid, the validated quiescent periods 88 may be used to determine motion compensation factors 106, as depicted at step 108. Determination of one or more motion compensation factors 106 may involve modeling the anticipated motion, based on the multi-input motion data 72 and/or quiescent periods 88, and calculating factors that compensate for the motion. Motion modeling can be accomplished either using the data directly or using a priori information about the moving organ. When motion is computed directly from the data, motion compensation factors 106 may be derived by an iterative algorithm trying to optimize criteria in multiple domains including the spatial and transform domains. When prior information is available, non-iterative methods can be used for determination of motion compensation factors 106.

Gating points 110 may be derived from the validated quiescent periods 88 at step 108 instead of, or in addition to, motion compensation factors 106. The gating points 110 typically describe the points in time from which acquired data is selected, for retrospective gating, or during which data acquisition occurs, for prospective gating. For example, referring to FIG. 3, gating points 110 may be selected which coincide with the beginning and end of the quiescent period 88 such that image data is acquired or selected at the beginning of the quiescent period 88 and is not selected or acquired after the end of the quiescent period 88. In this manner, image data is acquired or selected which corresponds to an interval of low or no motion for the organ of interest, such as the heart or lungs in this example. Reconstructed images of the organ or organs of interest, therefore, should be less susceptible to motion-related artifacts.

Figure 5:
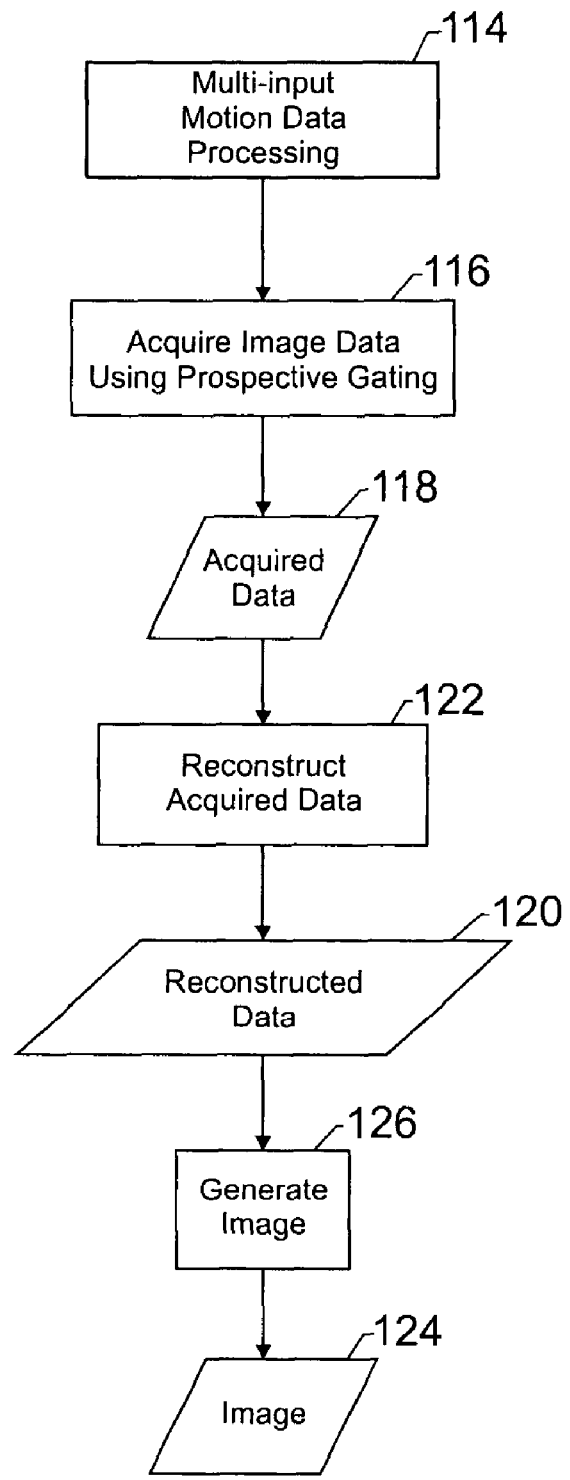
FIG. 5 is a flowchart depicting prospective gating, in accordance with the present technique.

The gating points 110 and motion correction factors 106 derived from the multi-input motion data 72 may be utilized by various image-processing techniques. For example, prospective gating points, i.e., gating points 110 used for prospective gating, may be utilized during an image acquisition process, as depicted in FIG. 5. The prospective gating points may be derived from multi-input motion data processing, as depicted at step 114.

The step 114 of multi-input motion data processing may include some or all of the steps and data described above with regard to FIGS. 2 and 4 and may represent a dynamic step that reflects the acquisition of motion information by sensor and/or image data-based methodologies prior to and/or during the image acquisition interval. The resulting set of multi-input motion data 72 may be processed at the dynamic processing step 114 to extract the desired quiescent periods 88, gating points 110, and/or motion correction factors 106. For example, in the case of cardiac imaging, electrical sensors 42 may be employed to detect the motion of the heart and/or lungs during or prior to image acquisition, allowing the determination of or prediction of prospective gating points. Furthermore, one or more mechanical sensors 46, such as accelerometers or displacement sensors may be employed in addition to or instead of electrical sensors 42 to detect the motion of the heart and/or lungs during or prior to image acquisition.

Similarly, image data-based techniques, such as pre-acquisition techniques, may be employed in addition to or instead of the sensor-based techniques to detect the motion of one or more of the organs of interest during or prior to image acquisition. In addition, acquisition data, either in reconstructed and/or unreconstructed domains, may be used for extrapolating a cycle of motion or for validating a phase of motion that may be useful in a prospective context. The resulting set of multi-input motion data 72 may, therefore, be used to determine quiescent periods 88, as discussed above, which may in turn be used to derive gating points 110 for use in the prospective gating of the image data acquisition of the one or more organs of interest.

Referring once again to FIG. 5, the prospective gating points determined by the multi-input motion data processing step 114 may be used to activate an imager 12 to acquire data 118 during the desired quiescent periods 88, or other period of interest, as depicted at step 116. The acquired data 118 may be reconstructed to form a set of reconstructed data 120, as depicted at step 122. The reconstructed data 122 may be further processed if desired, such as by segmentation of structure or features of interest, edge enhancement, smoothing, and so forth. An image 124 of the region of interest which contains a reduced number of motion related artifacts may be generated, as depicted at step 126. In addition, motion compensation factors 106 may be derived from the quiescent periods 88, or other periods of interest, which may be applied during data reconstruction at step 122 or image generation at step 126 to further reduce motion-related artifacts. Furthermore, image fusion may be implemented if multiple electrical and/or non-electrical sensors are employed, particularly in the context of multi-modality imaging. In such an image fusion context, motion data derived from the multi-input motion data set 72 may be combined with the image data in the image 124 to visually convey motion, acceleration, displacement, polarization, or some other sensed parameter in conjunction with structure.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method for imaging an organ, comprising the steps of:
    acquiring a set of motion data for one or more organs using one or more sensors configured to measure electrical or non-electrical activity indicative of motion of the one or more organs;
    validating the set of motion data using another set of motion data derived from a dataset acquired using an imager;
    processing the set of motion data to extract two or more prospective gating points for an organ of interest;
    acquiring a set of image data representative of the organ of interest using the two or more prospective gating points using the imager;
    reconstructing the set of image data to generate a set of reconstructed data; and
    generating an image from the set of reconstructed data, wherein generating the image comprises fusing a set of image data representative of structure with at least one of a set of image data representative of motion or a set of image data representative of electrical activity.

2. The method, as recited in claim 1, wherein at least one of the one or more sensors is activated in accordance with a set of positional data acquired by one or more positional sensors.

3. The method, as recited in claim 1, wherein the one or more sensors comprise two or more electrical sensors of the same type.

4. The method, as recited in claim 1, wherein the one or more sensors comprise at least one type of non-electrical sensor.

5. The method, as recited in claim 1, wherein the set of motion data is at least partially acquired from a set of pre-acquisition image data.

6. A method, for imaging an organ, comprising the steps of:
    acquiring a set of motion data for one or more organs using at least one electrical sensor and at least one non-electrical sensor configured to measure electrical or non-electrical activity indicative of motion of the one or more organs;
    processing the set of motion data to extract two or more prospective gating points for an organ of interest and to extract one or more motion compensation factors;
    acquiring a set of image data representative of the organ of interest using the two or more prospective gating points;
    reconstructing the set of image data to generate a set of reconstructed data; and
    generating an image from the set of reconstructed data, wherein generating the image comprises fusing a set of image data representative of structure with at least one of a set of image data representative of motion or a set of image data representative of electrical activity.

7. The method, as recited in claim 6, wherein at least one of the electrical or non-electrical sensors is activated in accordance with a set of positional data acquired by one or more positional sensors.

8. The method, as recited in claim 6, wherein the at least one electrical sensor comprises two or more electrical sensors of the same type.

9. The method, as recited in claim 6, wherein the at least one non-electrical sensor comprises one or more types of non-electrical sensors.

10. The method, as recited in claim 6, wherein the set of motion data is at least partially acquired from a set of pre-acquisition image data.

11. One or more non-transitory computer readable storage media having executable code stored thereon for imaging an organ, the executable code comprising:
    a routine for acquiring a set of motion data for one or more organs using one or more sensors configured to measure electrical or non-electrical activity indicative of motion of the one or more organs;
    a routine for validating the set of motion data using another set of motion data derived from a dataset acquired using an imager;
    a routine for processing the set of motion data to extract two or more prospective gating points for an organ of interest;
    a routine for acquiring a set of image data representative of the organ of interest using the two or more prospective gating points using the imager;
    a routine for reconstructing the set of image data to generate a set of reconstructed data; and
    a routine for generating an image from the set of reconstructed data, wherein the routine for generating the image fuses a set of image data representative of structure with at least one of a set of image data representative of motion or a set of image data representative of electrical activity.

12. The one or more computer readable storage media, as recited in claim 11, wherein the routine for acquiring the set of motion data activates at least one of the one or more sensors in accordance with a set of positional data acquired by one or more positional sensors.

13. The one or more computer readable storage media, as recited in claim 11, wherein the routine for acquiring the set of motion data acquires at least part of the set of motion data from a set of pre-acquisition image data.

14. One or more non-transitory computer readable storage media having executable code stored thereon for imaging an organ, the executable code comprising:

a routine for acquiring a set of motion data for one or more organs using at least one electrical sensor and at least one non-electrical sensor configured to measure electrical or non-electrical activity indicative of motion of the one or more organs;

a routine for processing the set of motion data to extract two or more prospective gating points for an organ of interest and to extract one or more motion compensation factors;

a routine for acquiring a set of image data representative of the organ of interest using the two or more prospective gating points;

a routine for reconstructing the set of image data to generate a set of reconstructed data; and a routine for generating an image from the set of reconstructed data, wherein the routine for generating the image fuses a set of image data representative of structure with at least one of a set of image data representative of motion or a set of image data representative of electrical activity.

15. The one or more computer readable storage media, as recited in claim 14, wherein the routine for acquiring the set of motion data activates at least one of the electrical or non-electrical sensors in accordance with a set of positional data acquired by one or more positional sensors.

16. The one or more computer readable storage media, as recited in claim 14, wherein the routine for acquiring the set of motion data acquires at least part of the set of motion data from a set of pre-acquisition image data.

17. An imaging system comprising:
an imager configured to generate a plurality of signals representative of a region of interest;
data acquisition circuitry configured to acquire the plurality of signals;
data processing circuitry configured to process the plurality of signals;
system control circuitry configured to operate at least one of the imager and the data acquisition circuitry;
an operator workstation configured to communicate with the system control circuitry and to receive the processed plurality of signals from the data processing circuitry; and
a sensor-based motion measurement system configured to measure electrical or non-electrical activity indicative of the motion of two or more organs within the region of interest using one or more sensors to obtain a set of motion data, wherein the one or more sensors comprises one or more non-electrical sensors, and wherein the imaging system comprises one or more positional sensors configured to activate the one or more non-electrical sensors based on the position of the one or more non-electrical sensors relative to the imager;
wherein the data processing circuitry is further configured to validate the set of motion data using another set of motion data derived from a dataset acquired by the imager.

18. An imaging system comprising:
an imager configured to generate a plurality of signals representative of a region of interest:
data acquisition circuitry configured to acquire the plurality of signals;
data processing circuitry configured to process the plurality of signals;
system control circuitry configured to operate at least one of the imager and the data acquisition circuitry;
an operator workstation configured to communicate with the system control circuitry and to receive the processed plurality of signals from the data processing circuitry; and
a sensor-based motion measurement system configured to measure electrical or non-electrical activity indicative of the motion of two or more organs within the region of interest using one or more sensors to obtain a set of motion data, wherein the one or more sensors comprises two or more electrical sensors, and wherein the imaging system comprises one or more positional sensors configured to activate the two or more electrical sensors based on the position of the two or more electrical sensors relative to the imager;
wherein the data processing circuitry is further configured to validate the set of motion data using another set of motion data derived from a dataset acquired by the imager.

19. The imaging system as recited in claim 18, wherein the one or more sensors comprises two or more electrical sensors, and wherein the sensor-based motion measurement system is configured to measure electrical activity indicative of the motion of the two or more organs via the two or more electrical sensors.

20. The imaging system as recited in claim 18, wherein the one or more sensors comprises one or more non-electrical sensors, and wherein the sensor-based motion measurement system is configured to measure non-electrical activity indicative of the motion of the two or more organs via the one or more non-electrical sensors.

21. The imaging system as recited in claim 20, wherein the one or more non-electrical sensors comprise accelerometers, optical markers, displacement sensors, force sensors, ultrasonic sensors, strain gauges, photodiodes, and pressure sensors.

22. An imaging system comprising:
an imager configured to generate a plurality of signals representative of a set of image data corresponding to a region of interest;
data acquisition circuitry configured to acquire the plurality of signals;
data processing circuitry configured to process the plurality of signals;
system control circuitry configured to operate at least one of the imager and the data acquisition circuitry based at least partially upon one or more motion compensation factors derived from a set of motion data describing the motion of two or more organs within a region of interest;
an operator workstation configured to communicate with the system control circuitry and to receive the processed plurality of signals from the data processing circuitry; and
two or more sensor-based motion measurement systems that contribute to the set of motion data, wherein the two or more sensor-based motion measurement systems include an electrical sensor-based motion measurement system configured to measure electrical activity indicative of the motion of the two or more organs and a non-electrical sensor-based motion measurement system configured to measure non-electrical activity indicative of the motion of the two or more organs;
wherein the data processing circuitry is configured to reconstruct the set of image data to generate a set of reconstructed data and generate an image from the set of reconstructed data by fusing a set of image data representative of structure with at least one of a set of image data representative of motion or a set of image data representative of electrical activity.

23. The imaging system as recited in claim 22, further comprising one or more positional sensors configured to activate one or more non-electrical sensors of the non-electrical sensor-based motion measurement system based on the position of one or more non-electrical sensors relative to the imager.

24. The imaging system as recited in claim 22, further comprising one or more positional sensors configured to activate two or more electrical sensors of electrical sensor-based motion measurement system based on the position of two or more electrical sensors relative to the imager.

25. The imaging system as recited in claim 22, wherein the electrical sensor-based motion measurement system is configured to measure electrical activity indicative of the motion of the two or more organs via two or more electrical sensors.

26. The imaging system as recited in claim 22, wherein the non-electrical sensor-based motion measurement system is configured to measure non-electrical activity indicative of the motion of the two or more organs via one or more non-electrical sensors.

27. The imaging system as recited in claim 26, wherein the one or more non-electrical sensors comprise accelerometers, optical markers, displacement sensors, force sensors, ultrasonic sensors, strain gauges, photodiodes, and pressure sensors.

28. An imaging system comprising:
an imager configured to generate a plurality of signals representative of a set of image data corresponding to a region of interest;
data acquisition circuitry configured to acquire the plurality of signals;
data processing circuitry configured to process the plurality of signals;
system control circuitry configured to operate at least one of the imager and the data acquisition circuitry based upon two or more prospective gating points derived from a set of motion data describing the motion of two or more organs within the region of interest;
an operator workstation configured to communicate with the system control circuitry and to receive the processed plurality of signals from the data processing circuitry; and
a sensor-based motion measurement system configured to measure electrical or non-electrical activity indicative of the motion of at least one of the two or more organs within the region of interest using one or more sensors to contribute to the set of motion data;
wherein the data processing circuitry is further configured to validate the set of motion data using another set of motion data derived from a dataset acquired by the imager, reconstruct the set of image data to generate a set of reconstructed data, and generate an image from the set of reconstructed data by fusing a set of image data representative of structure with at least one of a set of image data representative of motion or a set of image data representative of electrical activity.

29. An imaging system comprising:
an imager configured to generate a plurality of signals representative of a set of image data corresponding to a region of interest;
data acquisition circuitry configured to acquire the plurality of signals;
data processing circuitry configured to process the plurality of signals;
system control circuitry configured to operate at least one of the imager and the data acquisition circuitry based upon two or more prospective gating points and one or more motion compensation factors derived from a set of motion data describing the motion of two or more organs within a region of interest;
an operator workstation configured to communicate with the system control circuitry and to receive the processed plurality of signals from the data processing circuitry; and
a sensor-based motion measurement system configured to contribute to the set of motion data by measuring electrical or non-electrical activity indicative of the motion of the at least one organ within the region of interest using at least one electrical sensor and at least one non-electrical sensor;
wherein the data processing circuitry is configured to reconstruct the set of image data to generate a set of reconstructed data and generate an image from the set of reconstructed data by fusing a set of image data representative of structure with at least one of a set of image data representative of motion or a set of image data representative of electrical activity.

30. The imaging system as recited in claim 18, wherein the one or more sensors comprises two or more electrical sensors, and wherein the sensor-based motion measurement system is configured to measure electrical activity indicative of the motion of the two or more organs via the two or more electrical sensors.

31. The imaging system as recited in claim 18, wherein the one or more sensors comprises one or more non-electrical sensors, and wherein the sensor-based motion measurement system is configured to measure non-electrical activity indicative of the motion of the two or more organs via the one or more non-electrical sensors.

32. The imaging system as recited in claim 31, wherein the one or more non-electrical sensors comprise accelerometers, optical markers, displacement sensors, force sensors, ultrasonic sensors, strain gauges, photodiodes, and pressure sensors.

* * * * *